United States Patent [19]
Gevins

[11] Patent Number: 5,119,816
[45] Date of Patent: Jun. 9, 1992

[54] EEG SPATIAL PLACEMENT AND ENHANCEMENT METHOD

[75] Inventor: Alan S. Gevins, San Francisco, Calif.

[73] Assignee: Sam Technology, Inc., San Francisco, Calif.

[21] Appl. No.: 578,880

[22] Filed: Sep. 7, 1990

[51] Int. Cl.$^5$ .............................................. A61B 5/04
[52] U.S. Cl. ................................................. 128/644
[58] Field of Search ............... 128/639, 640, 644, 731, 128/732, 791, 845; 606/129, 130

[56] References Cited

U.S. PATENT DOCUMENTS

| | | | |
|---|---|---|---|
| 3,998,213 | 12/1976 | Price | 128/644 |
| 4,537,198 | 8/1985 | Corbett | 128/639 |
| 4,632,122 | 12/1986 | Johansson et al. | 128/664 |
| 4,844,086 | 7/1989 | Duffy | 128/731 |

FOREIGN PATENT DOCUMENTS 0355506  2/1990  European Pat. Off. ............ 128/731

*Primary Examiner*—Max Hinderburg
*Attorney, Agent, or Firm*—Eliot S. Gerber

[57] ABSTRACT

An improved brain wave electroencephalograph (EEG) method measures the physical positions of EEG electrodes applied to the subject's scalp. A set of standard cross-directional lines are obtained to provide measurements of the subject's head and a computer system automatically defines the subject's head shape according to predetermined head shape classes. The position of the electrode on the subject's scalp is then determined by scaling the measurements of the subject's head to a head model of the same head shape class.

4 Claims, 5 Drawing Sheets

EEG SPATIAL PLACEMENT AND ENHANCEMENT METHOD

BACKGROUND OF THE INVENTION

1. Field of Invention

The invention relates to brain wave medical systems and methods and more particularly to an electroencephalograph (EEG) system and method having improved spatial resolution.

2. Related Art

It is presently known that the brain waves of a human subject, at the microvolt level, may be amplified and analyzed using electroencephalograph (EEG) equipment. Generally 19 electrodes are electrically connected to the scalp of the subject and the brain waves are amplified and displayed in analog form. The U.S. Pat. No. 4,736,751, incorporated by reference, describes a system using a larger number of electrodes and various digital computer based methods to obtain more information from the brain wave signals.

However, when many electrodes are used, for example, 256 electrodes, it is time consuming to obtain their location on the subject's scalp using the conventional technique of tape measurements. If the subject is a child, senile or infirm, the subject may not be able to hold still for the 15-30 minutes which may be required for such measurements. The physical location of the electrodes is required to compare the EEG recordings, at each electrode, with the information obtainable concerning the head of the subject from other medical image systems, such as MRI (Magnetic Resonance Imaging).

The information produced from the EEG recordings may be made more clear and meaningful when the brain wave data is enhanced and analyzed by various methods executed in a digital computer system. However, the presently available methods do not provide sufficient spatial resolution for some purposes.

SUMMARY

A functional-anatomical brain scanner with a temporal resolution of less than a hundred milliseconds measures the neural substrate of higher cognitive functions, as well as diagnosing seizure disorders. Electrophysiological techniques, such as electroencephalograms (EEGs), have the requisite temporal resolution but their potential spatial resolution has not yet been realized. Progress in increasing the spatial detail of scalp-recorded EEGs and in registering their functional information with anatomical models of a patient's brain has been inhibited by the lack of a convenient means of rapidly placing many electrodes on the scalp, determining their location, determining the local thickness and conductivity of the scalp and skull, incorporating this information into a mathematical model, and using the mathematical model to enhance the spatial detail of the EEG signals. The three-dimensional positions of each electrode and the shape of the head are rapidly determined, the local thickness and conductivity of the skull and scalp are determined, and this information is used to reduce blur distortion of scalp-recorded EEGs, in effect mathematically placing the electrode just above the surface of the brain.

In accordance with one aspect of the present invention, a method is presented to improve the spatial resolution of electroencephalograph (EEG) medical images. The physical location of each of the electrodes in a large set of electrodes placed on the head of a subject is measured. A flexible hat is placed on the subject's head and piezoelectric ribbons, embedded in the hat are stretched. The ribbons are directed in cross-lines and the extent the ribbons are stretched (tensioned) determines the size of the subject's head in the direction along which the ribbon lies. The head measurements are entered into a pattern recognition computer system, preferably a neural network computer, and the subject's head shape is classified as falling into one class of head shapes. The electrode locations are mathematically derived in a computer system based on the known locations of the corresponding electrodes on a head model in the same head shape class and the size of the subject's head.

In another aspect of the present invention, the EEG spatial resolution is improved using information about the geometry and conductivity of the skull to remove distortion due to transmission from the brain to the scalp. This requires 1) Measuring the size and shape of the subject's head; 2) Measuring the local skull thickness using an ultrasonic source and analyzing the reflected waves from the skull; 3) Estimating the local conductivity of the skull; and 4) Using these measurements to correct the EEG signals for distortion.

BRIEF DESCRIPTION OF THE DRAWINGS

In the drawings

FIG. 1A shows the top view of the head, FIG. 1B shows the right side of the head, and FIG. 1C shows the left side of the head.

DETAILED DESCRIPTION

I. EEG Recording Method

A. Nomenclature for 256 Electrode Placements

Figure 1A:
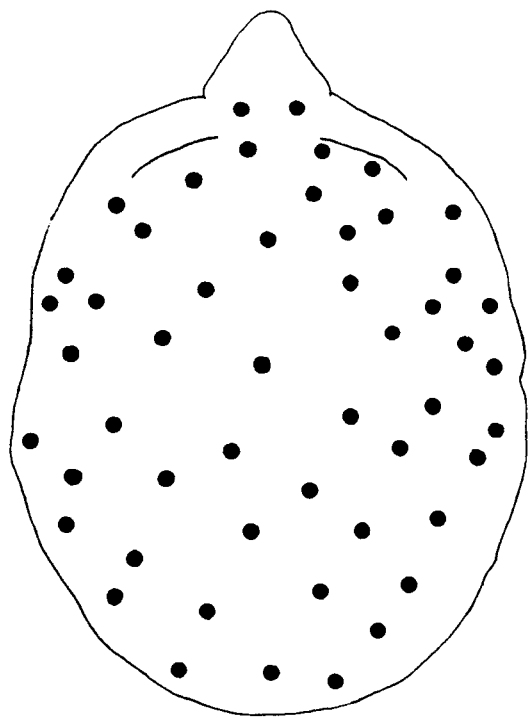
FIGS. 1A-1C are diagrams of a 124-channel scalp montage. Electrode names are based on 10-20 system with additional letter prefixes and numerical suffices.
Figure 1B:
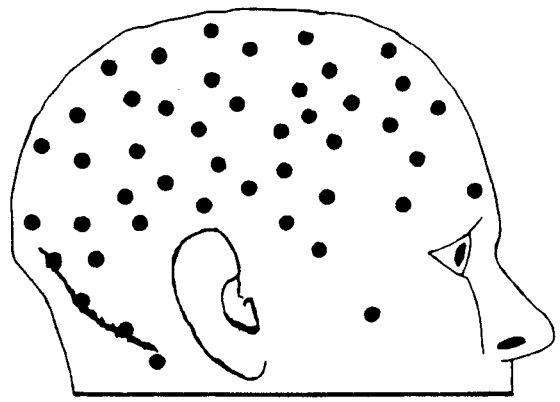
Figure 1C:
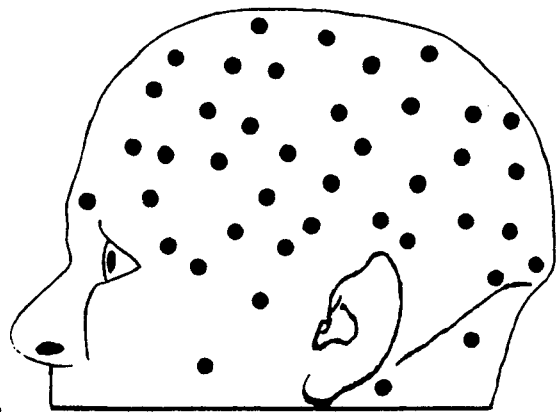

A nomenclature is defined for the extra equidistant coronal rows added between the original rows of the conventional International 10-20 System as well as the extra equidistant electrodes added to fill in the spaces in each row (FIGS. 1A-1C). For example, the preferred number of electrodes is 64-512 and most preferred are 256 scalp electrodes. The letter "a" is prefixed to the conventional 10-20 row name to indicate a position anterior to the existing one. For example aO is anterior occipital, aP is anterior parietal, aC is anterior central and aF is anterior frontal. Two additional numbers appear after the location number (1-8) of the 10-20 positions. These two numbers (0-9) indicate the proportional distance to the next anterior and medial 10% electrode position, respectively. For example, an electrode halfway between P3 and aP1 would be named P355, while an electrode halfway between P3 and P1 would be named P305. With the original nineteen electrodes of the 10-20 System, the typical distance between electrodes on an average adult male head is about 6 cm; with 124 electrodes, the typical distance is about 2.25 cm; with 256 electrodes, the typical distance is about 1 cm.

B. Smart EEG Hat

In most routine clinical EEGS, electrodes are prepared and positioned on the head individually, while in some labs commercially available electrode caps with up to 32 built-in electrodes are used. Extending this idea, we developed a more efficient system for recording up to 124 or more EEG channels with little or no preparation of the scalp, as described in U.S. Pat. No. 5,038,782, incorporated by reference herein.

C. Measuring Electrode Positions

Traditionally, individual electrodes are placed according to measurements taken with a tape measure. While this has been sufficient for qualitative examination of strip chart tracings with up to 21 electrodes, greater precision and a method using less time are needed when many more electrodes are used and when one wishes to relate a recording position on the scalp to the underlying brain anatomy.

Figure 2:
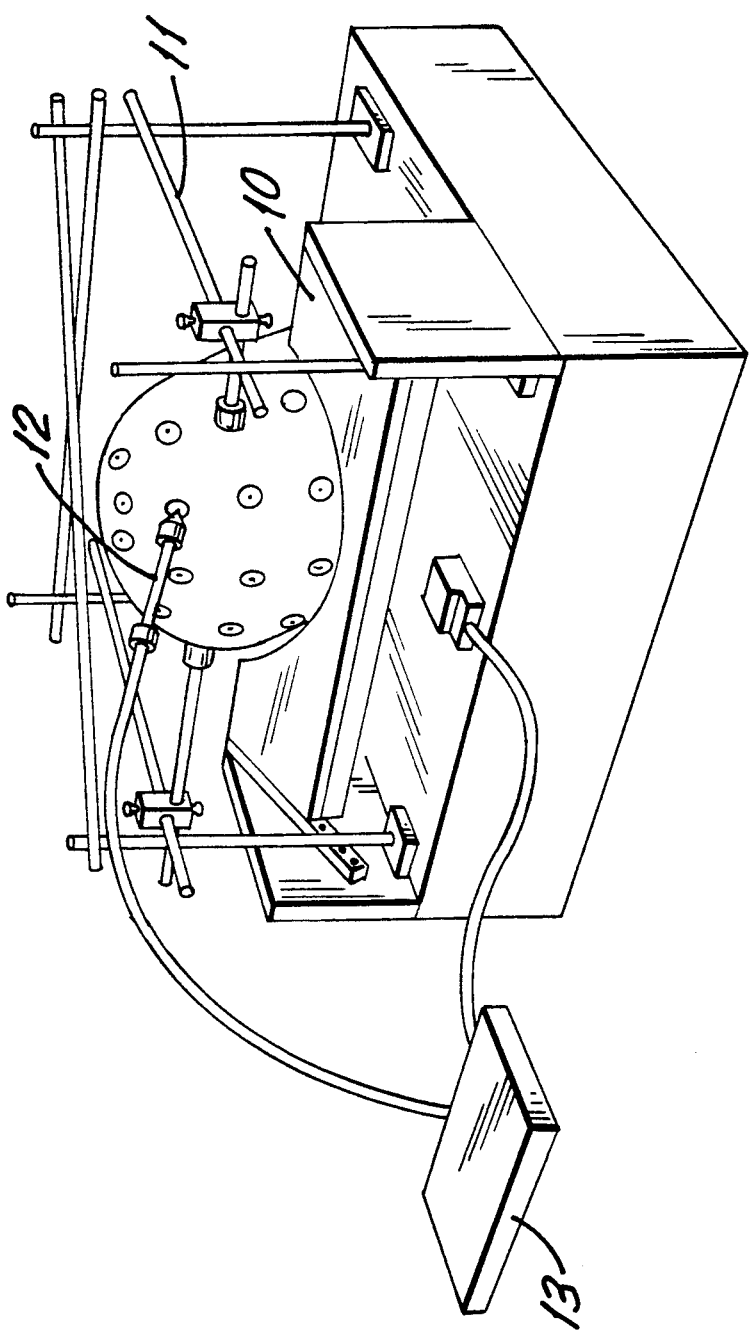
FIG. 2 is a perspective view of the apparatus used to measure the electrode coordinates. The research assistant touches each electrode with a magnetic position sensor which the subject is resting his head on a chin rest built into a head support which gently restricts head movement during the measurements. The 3-D coordinates of each electrode position are transmitted to the data collection computer.

In accordance with the present invention, the position of each electrode on a subject's head is measured with a probe 12, such as the 3-Space Isotrak digitizer by Polhemus Navigation Sciences, that has coils for sensing the three-dimensional position of the probe tip with respect to a magnetic field source attached to the head support 10 (FIG. 2). Adjustable guides 11 built into the head support hold the subject's head comfortably in place while the measurements are made. A menu-driven program on a control digital computer 13 is used to select electrodes to be measured and display the digitized position of each electrode on a two-dimensional projection display. Position measurement is accurate to better than 3 mm [RMS]. While this procedure provides greatly increased precision over the use of a tape, it can take fifteen minutes to measure the positions of 124 electrodes during which time the patient must keep his head still in the head support device. Such lack of motion for that time period may be difficult or impossible for very young or infirm patients.

An alternative procedure is to attache the transmitter for the Isotrak digitizer to the head with an adjustable elastic band, eliminating the need for the head support device. This alternative is more comfortable for the patient, but does not reduce the time required to measure each electrode.

Figure 3:
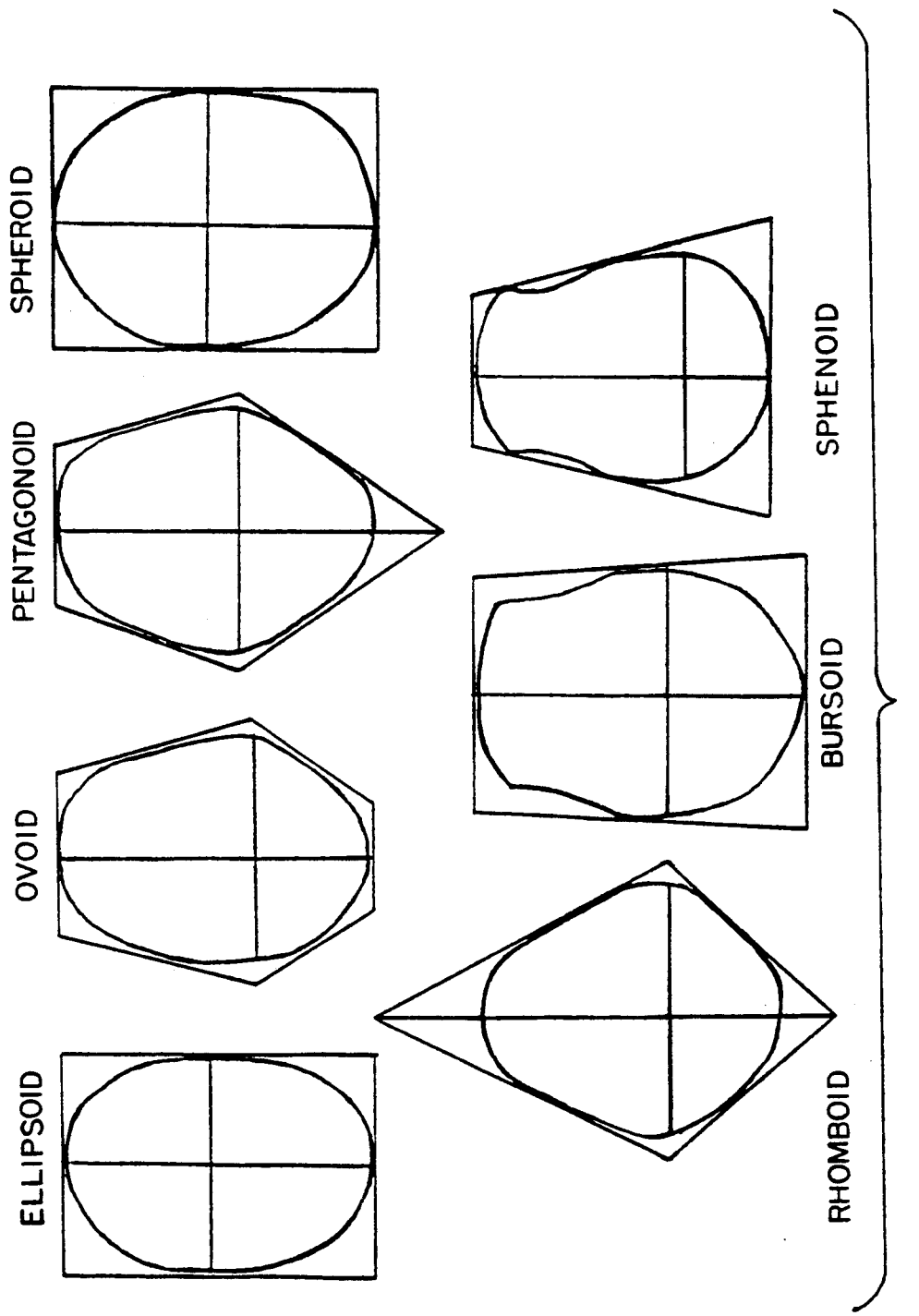
FIG. 3 shows the top views of seven representative head shapes.
Figure 4:
FIG. 4 shows output of automatic edge-detection software of a midline sagittal Magnetic Resonance Image (MRI) obtained with Tr-600 and TE-20 ms. The lines shown correspond to locations of local maxima in the gradient of the image intensity. These contours pass through the points at which the local average intensity is changing most rapidly.

In accordance with the present invention, in another alternate procedure, electrode positions are determined by classifying a subject's head shape as one of seven canonical head shapes (FIG. 3), determining a scale factor which is the size of the subject's head relative to an average sized head of that canonical shape, and estimating electrode positions as scaled values of the standard electrode positions for that particular canonical head. The patient's head shape is classified by: (1) measuring hat stretch of stretch hat 20 having elastic bands 21 at several points over the head using piezo-electric sensors 22 as ribbons embedded within the hat (see FIG. 6; (2) scaling the vector of stretch measurements, termed the "stretch vector," to have unit magnitude; and (3) feeding this vector to a neural network or other mathematical computer pattern classifier that has been trained to make the desired classification. The scaling factor is the ratio between the stretch vector magnitudes of the subject and that determined from a canonical head of average size. For each electrode montage provided with the hat and each canonical head shape, accurate measurements of electrode position are made on an average sized model of that head. Appropriately scaling these electrode positions gives a reasonably accurate estimate of actual electrode position and has the advantage that no additional time is added to the EEG recording session.

Another alternative procedure is to place a flexible grid of electric field sources in close proximity to the head and then measure the potential induced in each electrode when each node in the grid is activated. For example the nodes (electric field sources) may be resonant circuits or switch points which form a grid on a flexible cap. The relative position of each node is calculated by interpolation from the pattern of induced voltages. The grid may be embedded in a hat which fits over the hat containing the recording electrodes or the recording electrodes and field source may be combined. This has the advantage of increased precision with no significant increase in recording time.

D. Software System for EEG Analysis

Although commercial EEG computer systems have improved during the past few years, some important limitations still restrict their utility, including: (1) system capacity that is inadequate for recording large numbers of channels (124 or more) and collecting and storing large databases; and (2) spatial sampling and analyses that are inadequate, with too few channels, a lack of effective means to reduce volume conduction distortion, a lack of cross-channel analyses (e.g., crosscovariance and crosspower, correlation and coherence,), and a lack of means to investigate the relationship between neuroelectric data and cortical anatomy and physiology revealed by MRI and PET imaging technologies.

1. Data Collection

One or two computers are used for stimulus presentation and data collection. One computer is used to present stimuli and gather behavior response data from the subject while the other collects physiological data and controls the first computer. When a very fast computer is used, or not many channels are required, a single computer can be used to perform all operations. A control software system runs the two computers, presents a variety of visual, auditory and somatosensory stimuli to the subject according to flexible task protocols, and digitizes up to 256 channels of evoked brain wave physiological data. Up to 128 EEG traces can be monitored in real time as data are collected. Most parameters of an experiment can be altered via a menu-driven interactive display. A calibration module numerically adjusts the gain of all channels according to the magnitude of a calibration signal which is injected, under computer control, into each electrode. Another module detects gross artifacts and color-codes contaminated data such as eye movements, gross head and body movements and bad electrode contacts. Stimulus, behavior and physiological data are stored on hard disk according to a self-recording data description language, and archived to optical disk or magnetic tape. The data are immediately available to researchers at their desks using either remote terminals, or UNIX workstations via Ethernet and Network File System.

2. Data Analysis

For subsequent data analysis the system also has a number of other functional improvements over its predecessors including: (1) least-squares and 3-D spline Laplacian derivation estimation and spatial deblurring using finite element or integral methods to reduce volume conduction distortion; (2) digital filters with user-specified characteristics; (3) time series analysis including spectral analysis, Wigner Distributions (Morgan and Gevins, 1986), and event-related covariance analysis (Gevins et al., 1987, 1989; Gevins and Bressler, 1988); (4) neural-network-driven pattern recognition to extract optimal or near-optimal subsets of features for recognizing different experimental or clinical categories (Gevins, 1980, 1987; Gevins and Morgan, 1988); and (5) anatomical modeling to construct 3-D mathematical models of the brain and head from MRI to CT brain scans. Four on-line, interactive subsystems are used to examine and edit data for residual artifacts (on an individual channel basis if desired), sort data according to stimulus, response or other categories, perform exploratory data analysis, and produce three-dimensional graphics representations of the brain and head.

II. Brain Modeling Methods

Since commercial magnetic resonance image (MRI) analysis packages lack essential features for functional-anatomical integration studies, there is described below algorithms and a softward outline to produce 3-D brain models suitable for functional localization studies. Visualization software permits construction of 3-D composites of multiple 2-D image planes, as well as 3-D surface rendering based on surface contours. Since generating surface contours manually is laborious and subject to error, we have largely automated the procedure. We have also automated the alignment of the digitized EEG electrode positions with the scalp surface contours, which is a critical first step in a functional-anatomical analysis. The MRI contour information is used to produce mathematical finite element or surface integral models of the brain and head suitable for equivalent dipole source localization and scalp EEG deblurring procedures.

A. EEG-MRI Alignment Procedure

In order to visualize the brain areas underlying EEG electrodes, a procedure is needed for aligning scalp electrode positions with the MR Images. In our procedure, x, y, z translation and x, y, z axis rotations are computed iteratively to align the digitized positions of the EEG electrodes with the MRI data. This is done for each electrode by finding the distance to the closest point on the scalp surface MRI contours and minimizing the mean distance for all electrodes. With MR images that have a 3 mm inter-slice spacing, the mean error distance is usually better than 2 mm. This is more accurate and less subjective than alignment procedures that use skull landmarks such as the nasion and preauricular points located visually in the MR images. FIG. 1A shows the electrodes displayed schematically on a scalp surface reconstructed from horizontal MR scalp contours as described below.

B. 3-D Composite MRI Displays

In order to visualize how the individual MRI slices fit together to form a three-dimensional object, a means is needed to juxtapose an arbitrary number of slices from sagittal, coronal and horizontal scanning planes into a composite image, and view the juxtaposed slices from an arbitrary viewing angle.

C. Contour Extraction and External Surface Rendering

In order to visualize the external three dimensional surface of the brain and head, a means is needed to compute the curved surfaces from the information contained in the set of two-dimensional MRI slices. Scalp and cortical surface contours are extracted from MRIs using two image analysis methods we developed. The first technique used intensity thresholding, which involves extracting contours along which the image intensity is equal to a defined threshold. This technique is useful for extracting the scalp surface contour which can be discerned easily from the black (approximately zero intensity) background of the image. The technique has six steps: 1) for each pair of adjacent contours, find the point on the second contour closest to the first; 2) calculate the two distances from each of these points to the next point on the adjacent contour; 3) make a triangle using the point with the shortest distance, advancing on that contour; 4) repeat steps two and three until all points are exhausted; 5) repeat steps two to four in the reverse direction along the contours; and 6) piece together the "best" results.

Figure 6:
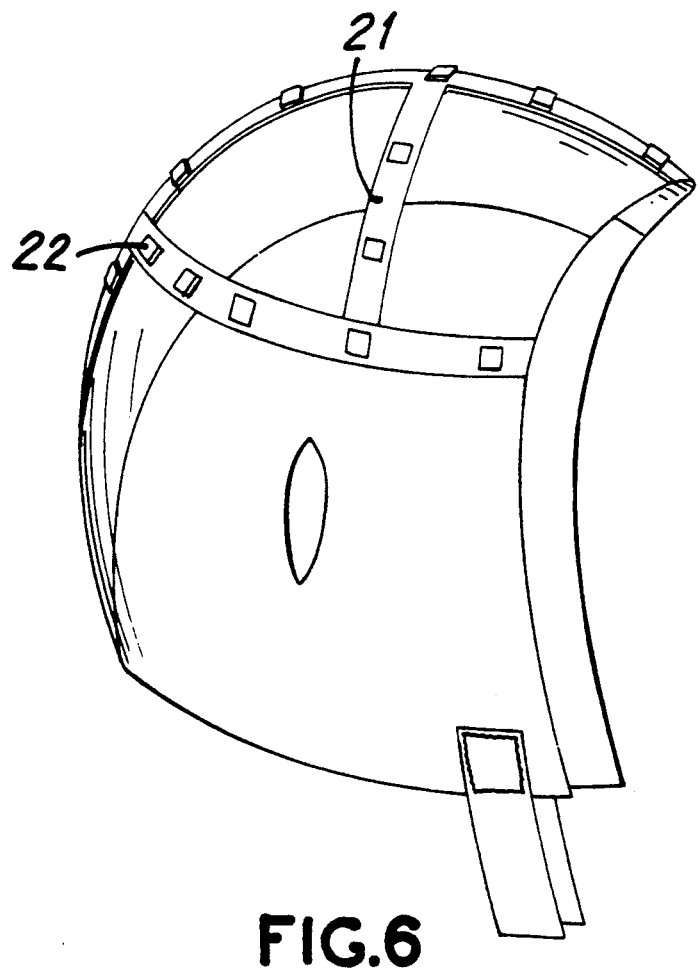
FIG. 6 is a perspective view of the flexible measurement hat having piezo-electric ribbons embedded therein.

The second contour extraction method involves differential intensity analysis. Using this technique, contours that separate image regions with different local average intensities are extracted. Resulting contours pass through the points in the image at which the local average image intensity is changing most rapidly. This technique requires no a priori intensity threshold value, and is useful for extracting the cortical surface contour which has a less well-defined image intensity value throughout an image than the scalp surface contour. The first-order and second-order partial derivatives of the image are estimated using 2-D filters, and these derivatives are used to locate the local maxima in the gradient of the image intensity. Highly computationally efficient filtering techniques have been developed for the estimation of the partial derivatives of the image (Algazi et al., 1989). FIG. 6 shows an example of contours corresponding to locations of local maxima in the gradient of the image intensity, which trace sulci.

D. 3-D Cortical Internal Surface Image Model 3-D surface models of the external convexity of the cerebral cortex are not sufficient to visualize and computationally model the cortical surface within fissures and sulci. As a result, we developed an algorithm to model cubic volume elements (voxels). The faces of the voxels lie in the horizontal, coronal, and sagittal planes for which MRI data have been obtained. The MRI data are mapped onto the faces of the voxels to obtain a 3-dimensional display of the image data. The image planes used are averaged horizontal planes that lie halfway between the horizontal planes in which MRI data have been acquired, and coronal and sagittal image planes (that can optionally be synthesized from the acquired horizontal images). The spacing between image planes is 3 mm, which yields voxels with dimensions of 3 mm by 3 mm by 3 mm. The images have pixel dimensions of approximately 1 mm by 1 mm.

The initial set of voxels is the set bounded by those voxels that lie just inside the cortical surface. To view the MRI data at a slightly deeper level, a mathematical morphology erosion operation is used to remove the boundary layer of voxels, thereby exposing the faces of the voxels that lie one layer deeper. By eroding the model iteratively, anatomical structures can be tracked and 3-dimensional models of the structures can be made (see FIG. 7).

E. 3-D Electrical Brain Model: Finite Element Method

A mathematical 3-D representation of the brain and head are needed to most effectively deblur the EEG recorded at the scalp and to compute equivalent current dipole sources from the scalp EEG. We developed an efficient finite element method for this purpose.

Maxwell's Equation, $$\nabla \cdot (\sigma \nabla u) + \nabla \cdot J = 0 \quad \text{in } \Omega \tag{1}$$

is frequently used to study the electromagnetic field generated by populations of neurons. Here $\sigma(>0)$ is the conductivity tensor at a point $=(x,y,z)$ in $\Omega$ (e.g., a human head), u is the electric potential at R, J is the electric current density at R and $\nabla$ is the grad vector operator. When $\Omega$ represents a human head, the following boundary condition for equation (1) is obtained $$\sigma \nabla u \cdot n = 0 \quad \text{on } S(\text{headsurface}) \tag{2}$$

since electric current does not flow out of the head in the direction normal to the surfaces. The limited scalp potential measurement specifies another boundary condition.

$$u = U(x,y,z) \quad \text{on } S_1. \tag{3}$$

Where $S_1$ is a subsurface of S corresponding to the area covered by the electrodes.

The Finite Element Method (FEM) we developed finds the numerical solution of equation (1) with the boundary condition as specified in equation (2) when the electromagnetic field activities of a head are modeled. Our implementation has the following special features:

a) A procedure to generate a list of wedges within a head such that each wedge has an unique tissue type and the interfaces between two neighboring wedges are perfectly matched to guarantee a correct numerical solution to Eq. (1).

b) A proper numbering scheme on a chosen set of nodes and the use of local supporting functions to produce a diagonally condensed block sparse coefficient matrix.

c) The use of elementwise local shape functions to represent the local supporting functions.

d) The use of a compressed data structure to obviate the need to allocate a very large memory space so that large size problems can be solved on desktop computer workstations.

e) Use of a C-language sparse matrix solver incorporating a temporary working array in the process of Cholesky Decomposition to speed up the process of computing the numerical solution.

Figure 5:
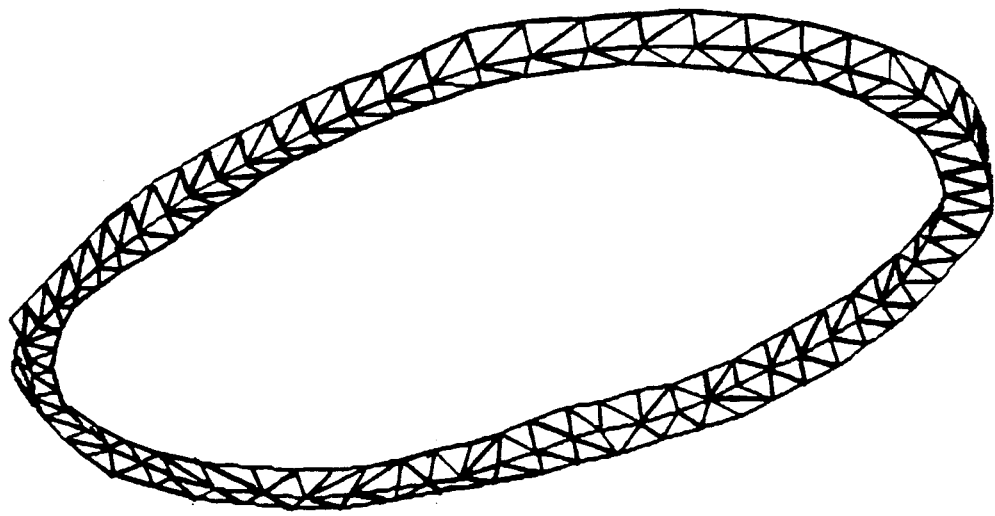
FIG. 5 shows automated construction of finite elements within brain, skull and scalp volumes, with terrahedral elements generated in an outer ring in brain.

Advantages of this approach are: 1) it handles the Dirac Delta Function $\nabla \cdot J$ smoothly by transforming equation (1) into a variational form when J represents a dipole-like kind of source; 2) it allows modeling of complicated geometries of different tissues within the head by generating finite elements using contours on pairs of adjacent MR images; and 3) it produces a sparse matrix in which many entries are zeros and thus is convenient and fast to compute on a desktop computer workstation. For example, a brain model with 10,087 FEM nodes can be solved in about 100 minutes on a SUN Sparc-1 workstation (12 MIPS) with 8 MB of memory (FIG. 5).

III. Spatial Enhancement Techniques to Reduce Blur Distortion

Electrical currents generated by sources in the brain are volume conducted through brain, cerebrospinal fluid, skull and scalp to the recording electrodes. The principal source of distortion in this process is produced by the skull, which has low conductance relative to the other tissues. Because of this spatial low-pass distortion, the potential distribution of a localized cortical source is spread over a considerable area of scalp and appears blurred or out of focus. For example, using a 4-shell spherical head model, we estimated the "point spread" for a radial dipole in the cortex to be about 2.5 cm. There are several methods to reduce this distortion which involve a tradeoff between the amount of information about head shape and tissue properties required versus the accuracy of the distortion correction.

A. Laplacian Derivation

The simplest method is the spatial Laplacian operator or Laplacian Derivation (LD). It involves computing the second derivative in space of the potential field at each electrode. This converts the potential into a quantity proportional to the current entering and exiting the scalp at each electrode site, and eliminates the effect of the reference electrode used during recording. An approximation to the Laplacian Derivation, introduced by Hjorth (1975, 1980) assumes that electrodes are equidistant and at right angles to each other. Although this approximation is fairly good for some electrode positions such as midline central (Cz), it is less accurate for others such as midtemporal (T5). We have developed two methods which produce more accurate estimates of the Laplacian using the actual measured electrode positions.

1. Planar Projection and Least Squares Solution

The first method is based on projecting the measured electrode positions onto a two-dimensional surface and estimating the surface Laplacian with a least-squares procedure.

The objective of the LD calculation is an accurate estimate of $$\left( \frac{\partial^2}{\partial x^2} + \frac{\partial^2}{\partial y^2} \right) V \tag{4}$$

Assume we wish to compute the LD at position $q_o$ using N surround electrodes in an arbitrary configuration. Let the voltage at position $q_i$ be designated by $V_i$. Put the origin of a cartesian coordinate system at $q_o$ with the z axis pointing perpendicular to the plane nearest the electrodes. Let $(q_{ix}, q_{iy})$ represent the x and y components of the electrode position within this plane.

Then $\vec{E}(x,y) = -\nabla V(x,y)$ is the electric field in the plane or equivalently:

$$V_0 - V_i = \int_C \vec{E} \cdot \vec{ds} \tag{5}$$

Where C is any curve in the plane connecting $q_o$ to $q_i$. If we let $E_x$ and $E_y$ designate the x and y components of $\bar{E}$ then the two-dimensional laplacian of the voltage is given by:

$$\nabla^2 V = -\left(\frac{\partial E_x}{\partial x} + \frac{\partial E_y}{\partial y}\right) \quad (6)$$

The field $\bar{E}$ can be expanded in a two-dimensional Taylor series (Rudin, 1976; Apostol, 1969) and expressed in a single matrix equation:

$$QF = V \quad (7)$$

In this equation the Q matrix is composed of the x and y coordinates electrode positions and remains fixed during the entire recording. The voltage vector V is measured at each time point and vector F composed of the electric field components and their derivatives is unknown.

Multiplying the above by the transpose of Q gives $$Q^T Q F = Q^T V \quad (8)$$

If Q premultiplied by its transpose $Q^T$ is nonsingular then we can form the least squares estimate of F as $$F = [Q^T Q]^{-1} Q^T V \quad (9)$$

If we let C be the sum of the third and fifth rows of $[Q^T Q]^{-1} Q^T$ then from the above equation we can estimate the laplacian LD as:

$$\nabla^2 V = -\left(\frac{\partial E_x}{\partial x} + \frac{\partial E_y}{\partial y}\right) \approx -CV \quad (10)$$

This method accounts for both variations in distance and variations in angle between electrodes in a computationally efficient manner, since once the coefficients are computed based on the positions of the electrodes, application of the method only requires a single matrix multiplication for each point of a time series. Although this procedure produces a dramatic improvement in topographic detail, some problems remain because of the projection onto a two-dimensional plane, and the assumption that the current gradient is uniform over the region encompassed by the surrounding electrodes used to estimate the Laplacian of an electrode.

2. Three Dimensional Spline Method

A more accurate method of estimating the Laplacian Derivation does not rely on the two-dimensional projection.

We compute the Laplacian of a distribution function U(x,y,z) (defined on a convex surface S) at its tangent plane attached to S at point $(x_0, y_0, z_0)$ where the surface S is defined by:

$$x = f(\xi, \eta); \; y = g(\mu, \eta); \; z = h(\xi, \eta)$$

We want to compute:

$$\frac{\partial^2 U}{\partial \xi^2} + \frac{\partial^2 U}{\partial \eta^2} \text{ at } \xi_0, \eta_0, \quad (11)$$

such that $$x_0 = f(\xi_0, \eta_0); \; y_0 = g(\xi_0, \eta_0); \; z_0 = h(\xi_0, \eta_0)$$

$(\xi_0, \eta_0)$ is a point in $\xi\eta$-plane. For convenience, we denote $\partial x/\partial \xi$ by $f_{86}$, etc. By the definition of the Laplacian here, f, g and h have to be the transformation functions for points on the $\xi\eta$-plane to points on the surface S defined in the current xyz-Cartesian coordinates. General forms of f, g and h for all points on $\xi\eta$-plane are difficult to find. However for every point $(x_0, y_0, z_0)$ on S, explicit forms of f, g and h can be found for translation and rotation transformations of points from $\xi\eta$-plane to the tangent plane of S at $(x_0, y_0, z_0)$ in xyz-Cartesian coordinates. The explicit form of the potential distribution function U(x,y,z) on a scalp surface S is not available in EEG recordings. However a set of scalp-recorded potential $V_i$ (i=1,2, ... n) is available on a set of recording channels on S, $(x_i, y_i, z_i)$, i=1,2, ..., n. Therefore the potential distribution can be computed by interpolation from the scalp-recorded potentials. First a set of basis functions $\phi_i(x,y,z)$ must be computed such that $$U(x,y,z) = \sum_1^n a_i \phi_i(x,y,z) \quad (12)$$

and $$U(x_i, y_i, z_i) = V_i \quad i = 1, 2, \ldots, n. \quad (13)$$

Since EEGs can be described by Maxwell's Equation, the open solution of that equation can be used for the basis functions. Accordingly, we define:

$$\phi_i(x,y,z) = \frac{1}{((x - x_{i0})^2 + (y - y_{i0})^2 + (z - z_{i0})^2)^{\frac{1}{2}}}. \quad (14)$$

Here $(x_{i0}, y_{i0}, z_{i0})$ is the center of the best fitting sphere of radius 1 to the point $(x_i, y_i, z_i)$ on the surface S. Algorithmically we choose this center point 1 unit from the i-th channel position $(x_i, y_i, z_i)$ in the opposite direction of the normal orientation of surface S at $(x_i, y_i, z_i)$. The basis function $\phi_i$ is a local support function and is smooth enough in the neighborhood of $(x_i, y_i, z_i)$. For a given channel list $(x_i, y_i, z_i)$ and its corresponding scalp potential data set $V_i$, (i=1,2, ..., n), we 1) construct a polygon montage spanned by these channels, that defines the surface S;
2) estimate the normal directions for every channel position by averaging the normal orientations of polygons surrounding this channel position;
3) construct a set of basis functions $\phi_i(x,y,z)$ and solve the weights $a_i$ through systems of equation in (13) by the Gaussian Elimination Method;
4) for every point on S, the desired surface tangent laplacian can be obtained by equations (11) and (12).

Equation (12) suggests that the desired surface tangent laplacian of U(x,y,z) can be computed by taking the surface tangent Laplacians of $\phi_i(x,y,z)$ for every point (x,y,z) on S, and then linearly combining them with weights $a_i$.

3. Finite Element Method

A better improvement in distortion correction is possible by using a Finite Element Method to represent the true geometry of cortex, cerebrospinal fluid, skull and scalp, and estimates of the conductivities of these tissues, to model the potential activity described by Maxwell's equations in the scalp and skull layers. This allows estimation of the potentials which would actually be recorded on the surface of the brain. This can be done without introducing an arbitrary model of the actual number and location of sources because, regardless of where they are generated in the brain, potentials recorded at the scalp must arise from volume conduction from the cortical surface through the skull and scalp.

We use Maxwell's equation and our Finite Element Method to relate the scalp-recorded potentials with the cortical potentials without introducing an explicit source function. For this application, the region of interest is limited to the scalp volume and skull volume. The difference between the inner surface of the skull and the outer convexity of the cortical surface is assumed to be small enough to be neglected. We also assume that the potential activity in the region of interest is described by Maxwell's equations, that the boundary condition on the air-scalp surface is stated by equation (2), i.e., current cannot flow out of the scalp, and that the boundary condition on the cortical surface is stated by the following equation which describes the cortical surface potentials:

$$u = G(x,y,z) \quad \text{on } S_2. \tag{15}$$

We also assume that there is no generating source within the scalp or skull which means the function J in equation (1) is zero. Although of course there is no general solution to the "inverse problem" because of the assumed boundary conditions there is a unique solution of equation (1), which may be obtained as follows. Applying the Finite Element Method to equation (1) with boundary conditions in (2) and (15), the following matrix vector relation is obtained:

$$Au = f. \tag{16}$$

Here u is a vector of dimension n, which is a numerical approximation to the analytical potential distribution function u in equation (1). The value of n corresponds to the total number of vertices on all the finite elements in the region of interest. Since we are assuming that no generating sources are present in the skull and scalp, $J=0$ and therefore $f=0$. We then decompose u into three sets, the potentials which correspond to the electrodes on the scalp, the potentials which correspond to the cortical surface, and the potentials in the rest of the region, and denote them by $u_1$, $u_3$ and $u_2$ respectively, If we decompose the matrix A correspondingly, then equation (16) becomes:

$$\begin{pmatrix} A_{11} & A_{12} & A_{13} \\ A_{21} & A_{22} & A_{23} \\ A_{31} & A_{32} & A_{33} \end{pmatrix} \begin{pmatrix} u_1 \\ u_2 \\ u_3 \end{pmatrix} = 0. \tag{17}$$

Solving $u_1$ with respect to $u_3$, we get $$(A_{11} - A_{12}A_{22}^{-1}A_{21})u_1 = (A_{12}A_{22}^{-1}A_{23} - A_{13})u_3 \tag{18}$$

and solving $u_3$ with respect to $u_1$, we get $$(A_{33} - A_{32}A_{22}^{-1}A_{23})u_3 = (A_{32}A_{22}^{-1}A_{21} - A_{31})u_1. \tag{19}$$

For a given $G_k$, $u_3^k$ is known. Then $u_1^k$ can be computed via equation (18) and the residual is calculated from $u_j^k$ and $U(x,y,z)$ which correspond to the predicted and measured potentials, respectively.

Equation (19) puts forward an alternative to the above approach. For each $u_1$, we can compute the cortical potential $u_3$. If there are a large number of recorded potential observations, such as hundreds of sampled time points, the following process will reduce the calculation time dramatically. Suppose $e_i$ is a vector of the same dimension as $u_1$ with all its components as zero except 1 at i-th position. Then $$u_1 = (s_1, s_2, \ldots, s_{n1})^t = \sum_1^{n_1} s_i e_i.$$

If we solve the $u_3$ in equation (19) with $u_1$ replaced by $e_i$ and denote the resulting solution vector by $p_i$, then for an arbitrary $u_i = (s_1, s_2, \ldots, s_{n1})^t$, the corresponding solution is:

$$u_3 = \sum_1^{n_1} s_i p_i$$

which is a simple linear combination of $n_1$ vectors and therefore much faster to compute.

4. Surface Integral Method

An alternative to performing deblurring (or dipole source localization) through using numerical solutions to the differential form of Maxwell's equations is to use numerical solutions to the integral form of Maxwell's equations.

The following equation is used for the source localization problem:

$$2\pi\sigma_{x_0}u - \sum_{i=1}^{J} \int_{s_i \rightrightarrows x_0} (\sigma_{i,out} - \sigma_{i,in}) \frac{\hat{n}_i \cdot \hat{R}}{R^2} u = \frac{\vec{R}_j \cdot \vec{J}}{R_j^3} \tag{20}$$

where $\sigma$ denotes conductivity; $\vec{x}_0$ is a point on the outer surface of the scalp, u is potential; $\vec{R}_j$ is the vector from a source to $\vec{x}_0$ and $R_j$ is its magnitude; $\vec{J}$ is the moment of a dipole source; 1 is the number of interfaces, $S_i$, between regions differing in conductivity; $n_i$ is the unit vector from the in region to the out region; and $\hat{R}$ is the vector from $\vec{x}_0$ to the point of integration with R denoting the unit vector and R denoting the magnitude. A numerical solution of this equation involves obtaining a discrete approximation to the integral. Boundary element methods can be used to do this. An alternative is to use efficient integration methods that have been developed for the sphere and methods of computational geometry for projecting a non-spherical surface on a sphere.

One advantage of using the integral method for source localization is that no nodes are close to the sources, a locus where potential fields vary a great deal. This is a problem for the finite element method.

The following equation is used for the deblurring problem:

$$\sum_{i=1}^{J} \int_{s_i \rightrightarrows x_0} (\sigma_{i,out} - \sigma_{i,in}) \frac{\hat{n}_i \cdot \hat{R}}{R^2} u = 2\pi\sigma\vec{x}_0 u \tag{21}$$

where the notation is that for Equation (20). After regularization, the numerical integration techniques used for source localization are applied. An advantage of this formulation when applied to deblurring is that it accounts for the geometry of the whole conductor whereas the finite element technique only accounts for the portion of the conductor that includes the electrodes on the scalp and the tissue immediately below.

5. Estimating Scalp and Skull Thickness for Models

In the finite element or surface integral methods, the local geometry of scalp and skull are each explicitly represented. If an MRI or CT brain scan is not available, an alternative method of measuring tissue thickness can be used based on low-frequency ultrasound technology.

For a low-resolution representation of skull thickness, the "end echo" in standard echoencephalography is used to estimate the thickness of the skull. This requires placing the ultrasonic probe at a position on the opposite side of the head from the place of desired measurement, normal to the scalp at the probe, and normal to the skull at the place of skull thickness measurement on the opposite side of the head from the probe. Skull thickness at each of the major cranial bones is measured in the following locations:

| cranial bone | position | probe position |
|---|---|---|
| left temporal | T3 | near T4, directly above the ear |
| right temporal | T4 | near T3, directly above the ear |
| frontal (left) | aF1-aF3 | roughly 1 cm below O2 |
| frontal (right) | aF2-aF4 | roughly 1 cm below O1 |
| left occipital | O1 | .2-.5 cm right of FPZ |
| right occipital | O2 | .2-.5 cm left of FPZ |
| left parietal | aP3 | 1 cm below M2, with upward tilt |
| right parietal | aP4 | 1 cm below M1, with upward tilt |

The end-echo consists primarily of the echo due to reflection from soft-tissue to inner skull interface and the echo due to outer skull to scalp interface (followed by a very small scalp-to-air echo). The delay prior to the end-echo varies, according to scalp location and inter-subject variation, roughly from 90 to 120 microseconds. The delay between the echos from either surface of the skull may vary from 1.7 to 5 microseconds. The second echo is attenuated with respect to the first, and requires a gain increase of 2.5 dB per MHz (typical) to be comparable in size to the first. Pulse widths of 0.25 to 1 microseconds are used with burst frequencies of 2 to 10 MHz, adjusted to produce the best discrimination between the two echos.

As necessary, passive receptors are used to scan the area of the intended skull thickness measurement to determine the accuracy of aim of the transmitted beam. When necessary, an average is taken over a small cluster of locations (3 to 6) near the listed probe site, in order to average over the variations in thickness for a given bone near the target area. In those instances when the aimed beam cannot be focused well on the parietal bones, the average thickness of these bones is estimated from normalized data on the relationship between parietal bone thickness and the average thickness of the other bones.

For finer spatial resolution in measurement of skull thickness, a near side detector can be used. It has two to four transmitters adjacent to the transmitter/receiver probe, spaced far enough away so that the critical angle (27 degrees) prevents energy from the adjacent transmitters from entering the skull at an angle that could be reflected back to the probe.

The phase and time delay between the adjacent transmitters and the probe is adjusted to minimize the reverberation at the probe. Thus, at the probe site the adjacent transmitters are contributing energy solely through reflections from the outer skull surface, and in a way to minimize reverberation at the probe. Only energy transmitted by the probe itself can enter the skull and be reflected back to the probe.

The thickness of the near skull can then be measured either by subtracting independent measures of the reflection time from the outer skull surface (adjacent transmitters inactive) and reflection time of the echo from the inner skull surface (reverberation minimization active), or by interferometry. The interferometry option sweeps the sound frequency (readjusting reverberation minimization for each frequency), and determines the change in frequency required for one oscillation in the variation in reflected energy due to interference of the inner and outer reflections from the skull. The measured thickness of the skull is one half the speed of sound in the skull divided by the change in frequency required to move through one "interference fringe".

6. Estimating Conductivities

Up to now, estimates of conductivity for the scalp, skull, CSF and brain have been from published sources (Geddes & Baker, 1967; Hosek, 1970). More accurate values are needed to realize the full benefit of the FEM head model. This can be done by solving for the ratio of skull-to-scalp and skull-to-brain conductivities using the scalp potential distribution produced by a single compact population of neurons, represented as an equivalent current dipole, whose location is approximately known. In one procedure, a steepest-descent, non-linear, least-squares fit between the measured potentials and the forward solution of an equivalent current dipole in a three-sphere model is performed (Fender, 1987). The main unknown parameters are the ratios of conductivities of the tissues, as well as the dipole strength (which is not of interest here). The availability of reasonable initial guesses, as well as upper and lower bounds, from existing experimental data result in realistic solutions for the unknown parameters. A highly localized source suitable for this purpose is the somatosensory evoked potential peak at 20 msec produced by mild stimulation of the contralateral median nerve at the wrist. This potential, negative posterior to the central sulcus and positive anterior to it, is generated by a single compact population of neurons oriented tangentially in the hand area of somatosensory area 3b and located about 2.5-3.0 cm below the surface of the scalp. Published values of the amplitude of the cortical potential and the ratio of cortical to scalp potentials are also available (Dinner et al., 1983). The global conductivity parameter is then adjusted for each of the finite elements in the skull using local skull thickness measures determined from the low frequency ultrasound, MRI or other means.

An alternative method for estimating tissue conductivity is based on measuring the reverse electromotive force produced by eddy currents induced in the tissue by an applied external field generated by a coil placed against the head of each patient. The magnitude of this emf depends on the conductivity of the tissue and the frequency of the magnetic field, i.e. higher conductivity means more eddy current is induced which gives a larger reverse emf. Very low frequencies induce eddy currents in all tissues whereas high frequencies induce currents only in the tissues closest to the coil. Scanning a spectrum of frequencies yields data from which the conductivities of each tissue type can be computed.

IV. Source Localization

We have also used FEM to: 1) localize single equivalent dipole sources of recorded scalp potentials; 2) obtain the potential distribution within the whole head given the localized source. We choose a specific function J and solve the corresponding potential distribution u using FEM such that the difference between u on $S_1$ and $U(x,y,z)$ defined on $S_1$ is minimized. The following source localization procedure (SLP) outlines an iterative process used to find J and u. For a chosen $J_0$ and $K=0, 1, 2, \ldots$, repeat the following: 1) find the numerical solution $u_k$ of equation (1) on $\Omega$ coupled with the boundary condition in equation (2) using FEM; 2) measure the difference between $u_k$ and $U(x,y,z)$ on $S_1$ and choose $J_{k+1}$; 3) compute the distance between $J_k$–$J_{k+1}$. If the distance is less than some tolerance, stop the loop. We applied the SLP to the case that J represents a single dipole. We used the Simplex algorithm (Nelder and Mead, 1965) for computing $J_{k+1}$.

LITERATURE CITED

[1] Algazi, V. R., Reutter, B. W., van Warmerdam, W. L. G & Liu, C. C. Three-dimensional image analysis and display by space-scale matching of cross sections. *J. Opt. Soc. Am.*, 1989; 6, 890-899.

[2] Apostol, T. M. *Calculus, Volume II, Multiple-Variable Calculus and Linear Algebra with Applications to Differential Equations and Probablility.* Xerox College Publishing. Waltham, Mass., 1969: 269-271.

[3] Dinner, D. S., Leuders, A. H., Lesser, R. P., Morris, H. H. & Hahn, J. (1983) Definition of rolandic fissure by cortical stimulation and somatosensory evoked potentials. Paper presented at 15th Epilepsy Society International Symposium.

[4] Fender, D. H., (1987), "Source localization of brain electrical activity", in Gevins, A. S. & Remond, A. (Eds.), *Methods of Analysis of Brain Electrical and Magnetic Signals, Vol. 1: Handbook of Electroencephalography and Clinical Neurophysiology,* Amsterdam, Elsevier, pp355-404.

[5] Geddes, L. A. & Baker, L. E. The specific resistance of biological material—a compendium of data for the biomedical engineer and physiologist. *Med. Biol. Engr.,* 1967: 5, 271-293.

[6] Gevins, A. S. Statistical pattern recognition. In A. Gevins & A. Remond (Eds.), *Methods of Analysis of Brain Electrical and Magnetic Signals: Handbook of Electroencephalography and Clinical Neurophysiology (Vol. 1),* Amsterdam, Elsevier, 1987.

[7] Gevins, A. S. Application of pattern recognition to brain electrical potentials. *IEEE Trans. Pattern Ana. Mach. Intell.,* 1980: PAM-12, 383-404.

[8] Gevins, A. S. and Bressler, S. L. Functional topography of the human brain. In: G. Pfurtscheller (Ed.), *Functional Brain Imaging.* Hans Huber Publishers, Bern, 1988: 99-116.

[9] Gevins, A. S. and Morgan, N. H. Applications of neural-network (NN) signal processing in brain research. *IEEE ASSP Trans.,* 1988: 7, 1152-1161.

[10] Gevins, A. S., Bressler, S. L., Morgan, N. H., Cutillo, B. A., White, R. M., Greer, D. & Illes, J., (1989), "Event-related covariances during a bimanual visuomotor task, I. Methods and analysis of stimulus- and response-locked data." *EEG Clin. Neurophysiol.,* v74, pp58-75.

[11] Gevins, A. S., Morgan, N. H., Bressler, S. L., Cutillo, B. A., White, R. M., Illes, J., Greer, D. S. & Doyle, J. C. (1987) Human neuroelectric patterns predict performance accuracy. *Science,* 235, pp. 580-585.

[12] Hjorth, B. An on-line transformation of EEG scalp potentials into orthogonal source derivations *Electroenceph. clin. Neurophysiol.,* 1975: 39, 526-530.

[13] Hjorth, B. Source derivation simplifies topographical EEG interpretation. *Amer. J. EEG Technol.,* 1980: 20, 121-132.

[14] Hosek, A. R. *An experimental and theoretical analysis of effects of volume conduction in a nonhomogeneous medium on scalp and cortical potentials generated in the brain.* Doctoral dissertation, Marquette Univ. Biomed. Engr., 1970.

[15] Morgan, N. H. & Gevins, A. S. (1986) Wigner distributions of human event-related brain potentials.B *IEEE Trans. Biomed. Enginr.,* BME-33 (1), pp. 66-70.

[16] Nelder, J., Mead, R. (1965) A simplex method for function minimization. *Computer Journal* 7, 308.

[17] Rudin, W. Principles of Mathematical Analysis. McGraw-Hill, New York, 1976: 243-244.

[18] Rogers, S. (1984) The Human Skull, Its Mechanics, Measurements, and Variations, p.75.

I claim:

1. The method of measuring the positions of a plurality of electroencephalographic (EEG) electrodes removably electrically connected to the head of a subject by:

(a) measuring the head of the subject by measuring a plurality of standard cross-directional lines on the head to obtain a set of head measurements;

(b) entering the set of head measurements into a computer system which automatically determines the classification of the head shape according to a plurality of predetermined head shape classes;

(c) comparing the subject head size to a predetermined head model of the same class in which the position of electrodes corresponding in position to the electrodes to be measured have been determined; and (d) determining the position of the electrodes connected to the head of the subject by scaling the measurements of the electrode positions on the head of the subject in accordance with the determined electrode positions of said head model.

2. The method of claim 1 wherein the measurements of step (a) are obtained by using a stretchable hat having piezoelectric ribbons embedded therein.

3. The method of claim 2 wherein the measurements are stretch measurements obtained from stretching of the ribbons and including the steps of obtaining a vector of said stretch measurements and scaling said stretch measurements.

4. The method of claim 1 wherein said computer system is a pattern recognition neural network computer.

* * * * *